United States Patent [19]

Wallhäusser et al.

[11] Patent Number: 4,920,151

[45] Date of Patent: Apr. 24, 1990

[54] MICROBICIDAL AGENTS BASED ON ALKYL-DI-GUANIDINIUM SALTS

[75] Inventors: Karl H. Wallhäusser, Hofheim am Taunus; Martin Hille, Liederbach; Hans-Walter Bücking, Kelkheim; Manfred Hofinger, Burgkirchen, all of Fed. Rep. of Germany

[73] Assignee: Hoechst Aktiengesellschaft, Frankfurt am Main, Fed. Rep. of Germany

[21] Appl. No.: 157,068

[22] Filed: Feb. 2, 1988

Related U.S. Application Data

[63] Continuation of Ser. No. 902,166, Aug. 29, 1986.

[30] Foreign Application Priority Data

Sep. 3, 1985 [DE] Fed. Rep. of Germany ........ 3531356

[51] Int. Cl.$^5$ ..................... A01N 33/12; A01N 37/52
[52] U.S. Cl. ....................... 514/634; 514/642
[58] Field of Search ................... 514/634, 642

[56] References Cited

FOREIGN PATENT DOCUMENTS

| | | |
|---|---|---|
| 1106277 | 4/1981 | Canada . |
| 0003999 | 2/1979 | European Pat. Off. . |
| 60-28906 | 2/1985 | Japan ................................. 514/634 |
| 1156517 | 6/1967 | United Kingdom . |

*Primary Examiner*—Allen J. Robinson

[57] ABSTRACT

The microbicidal agents consist esentially of 5 to 50% by weight of the salt of an alkyl-di-guanidine of the formula

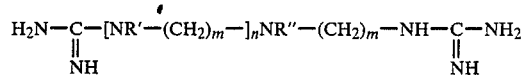

in which R' and R" denote hydrogen or $C_8$–$C_{18}$-alkyl, and R' and R" may not simultaneously be hydrogen, m denotes a number from 2 to 6 and n denotes 0 to 1, 5 to 50% by weight of a quaternary ammonium compound of the formula

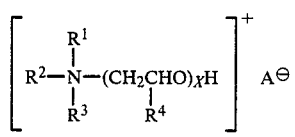

in which $R^1$ denotes $C_8$–$C_{22}$-alkyl or $C_8$–$C_{22}$-alkenyl, $R^2$ and $R^3$ denote $C_1$–$C_4$-alkyl or $C_2$–$C_3$-hydroxyalkyl and $R^4$ denotes hydrogen or methyl, or $R^1$ and $R^2$ denote $C_8$–$C_{12}$-alkyl, $R^3$ denotes $C_1$–$C_4$-alkyl or $C_2$–$C_3$-hydroxyalkyl and $R^4$ denotes hydrogen or methyl, X in both cases denotes a number from 1 to 3, preferably from 1 to 2 and in particular 1,5, and $A^\ominus$ denotes an anion of a carboxylic acid from the group comprising propiionic acid, lactic acid, glycolic acid, tartronic acid, malic acid, tartaric acid, citric acid, maleic acid and benzoic acid, and, as the remainder, water and/or a lower alcohol or a water-soluble glycol.

2 Claims, No Drawings

MICROBICIDAL AGENTS BASED ON ALKYL-DI-GUANIDINIUM SALTS

This application is a continuation of application Ser. No. 06/902,166 filed Aug. 29, 1986 entitled Microbicidal Agents based on Alkyl-Bi-Guanidinium Salts, now abandoned.

It is already known that alkyl-di-guanidinium salts have a good bactericidal and fungicidal action (German Patent C-1,249,457). Their possible use is limited, however, because, in some cases, their solubility in water is unsatisfactory and they have a poor compatibility, especially with hard water or water containing sodum chloride.

To improve the solubility and stability in water containing sodium chloride or hard water, it is already known that they can be combined with quaternary ammonium compounds or phosphonium compounds or with fatty alkyldiamine salts. However, it is a disadvantage here that the microbicidal action of the alkyl-di-guanidinium salts is adversely influenced by these emulsifiers. It is furthermore known (European Patent A-3,999) that combinations of alkyl-di-guanidinium salts and polyoxyethylene/polyoxypropylene block polymers give stable formulations with an improved microbicidal action. Such formulations have, however, an inadequate pour point.

The invention relates to novel, improved microbicidal agents consisting essentially of 5 to 50, preferably 20 to 30, % by weight of the salt of an alkyl-di-guanidine of the formula

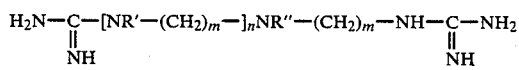

in which R' and R" denote hydrogen or $C_8$–$C_{18}$-alkyl, and R' and R" may not simultaneously be hydrogen, m denotes a number from 2 to 6 and n denotes 0 or 1, 5 to 50, preferably 20 to 30, % by weight of a quaternary ammonium compound of the formula

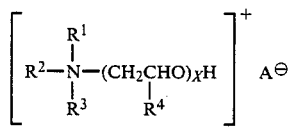

in which $R^1$ denotes $C_8$–$C_{22}$-alkyl or $C_8$–$C_{22}$-alkenyl, $R^2$ and $R^3$ denote $C_1$–$C_4$-alkyl or $C_2$–$C_3$-hydroxyalkyl and $R^4$ denotes hydrogen or methyl, or $R^1$ and $R^2$ denote $C_8$–$C_{12}$-alkyl, $R^3$ denotes $C_1$–$C_4$-alkyl or $C_2$–$C_3$-hydroxyalkyl and $R^4$ denotes hydrogen or methyl, X in both cases denotes a number from 1 to 3, preferably from 1 to 2 and in particular 1.5, and $A^\ominus$ denotes an anion of a carboxylic acid from the group comprising propionic acid, lactic acid, glycolic acid, tartronic acid, malic acid, tartaric acid, citric acid, maleic acid and benzoic acid, and, as the remainder, water and/or a lower alcohol or a water-soluble glycol.

Preferred quaternary ammonium compounds are those in which $R^1$ denotes $C_{12}$–$C_{18}$-alkyl or $C_{12}$–$C_{18}$-alkenyl, $R^2$ and $R^3$ denote methyl and $R^4$ denotes hydrogen, or $R^1$ and $R^2$ denote $C_8$–$C_{12}$-alkyl, $R^3$ denotes methyl and $R^4$ denotes hydrogen, and $A^\ominus$ denotes the anion of propionic acid, benzoic acid or lactic acid.

The alkyl-di-guanidines used can be prepared by processes which are already known, for example by reaction of diamines of the formula

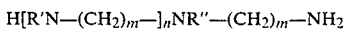

in which R', R", m and n have the abovementioned meaning, with cyanamide or S-alkylisothio urea.

Both mono- or polybasic inorganic or organic acids, for example sulfuric acid, nitric acid, phosphoric acid, formic acid or hydrochloric acid, are suitable for salt formation. Organic acids, such as, for example, acetic acid, propionic acid, lactic acid and also higher molecular weight aliphatic carboxylic acids, such as, for example, lauric acid, stearic acid, oleic acid and the like, or mixtures thereof, can also furthermore be used for salt formation. Instead of uniform individual compounds, it is also possible for mixtures of the compounds mentioned to be used, if appropriate also together with other microbicides. The quaternary ammonium compounds described above can be prepared by processes which are known per se, such as are described, for example, in German Patent A-3,319,509.

The microbicidal agents according to the invention, which are prepared by simply mixing the components described, are distinguished by a good water-solubility and are readily compatible with hard water or water containing sodium chloride. The improved microbicidal action in comparison with the previously known formulations containing quaternary ammonium compounds is to be particularly emphasized. It should furthermore be mentioned that the mixtures according to the invention have a low pour point (below $-40°$ C.). This means that they can be employed, in particular, in cold regions. These formulations moreover show an improved corrosion effect in comparison with conventional quaternary ammonium compounds. In particular, commercially available quaternary ammonium chlorides have powerful corrosive properties against the customary metals, such as, for example, iron, steel, V2A and V4A.

The following examples serve to illustrate the invention:

EXAMPLE 1

25 parts of coconut propylenediamine-di-guanidinium diacetate
25 parts of didecyl-methyl-hydroxyethyl-ammonium propionate
30 parts of isobutanol
15 parts of polyethylene glycol
5 parts of water This formulation is stable under the conditions of the swing test. It can be further diluted with water in any ratio to give a clear solution. The pour point is below $-50°$ C. The microbicidal effects can be seen from the table.

EXAMPLE 2

25 parts of coconut propylenediamine-di-guanidinium acetate
25 parts of didecyl-methyl-hydroxyethyl-ammonium propionate
20 parts of isobutanol
20 parts of glycol
5 parts of isopropanol
The results are comparable with Example 1.

EXAMPLE 3

25 parts of coconut propylenediamine-di-guanidinium diacetate 25 parts of didecyl-methyl-hydroxyethyl-ammonium propionate 25 parts of glycol 25 parts of isobutanol The results are comparable with Example 1.

EXAMPLE 4

25 parts of the bisguanidinium derivative of the formula

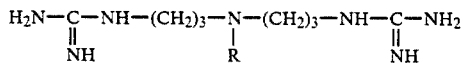

R = coconut alkyl 25 parts of didecyl-methyl-hydroxyethyl-ammonium propionate 25 parts of isopropanol 25 parts of glycol The results are comparable with Example 1.

EXAMPLE 5

25 parts of coconut propylenediamine-di-guanidinium diacetate 25 parts of didecyl-methyl-hydroxyethyl-ammonium propionate 50 parts of polyglycol 400.

EXAMPLE 6

25 parts of coconut propylenediamine-di-guanidinium acetate 25 parts of soya alkyl-dimethyl-hydroxyethyl-ammonium propionate 37 parts of isobutanol 100 parts of glycol/water

COMPARISON PRODUCT (COMMERCIALLY AVAILABLE)

25 parts of coconut propylenediamine-di-guanidinium diacetate 25 parts of soya-trimethyl-ammonium chloride 25 parts of isopropanol 25 parts of water

RESULT

The comparison product can readily be diluted with water, but in comparison with Examples 1 to 6 according to the invention the microbicidal effects are reduced. The low temperature turbidity point (pour point) is inadequate.

The microbicidal action was tested by the quantitative suspension test. A detailed description of the experimental procedure can be found in the literature (Zbl. Bakt. Hyg. I Abt. Orig. B 165, 355–380, 1977).

| | Quantitative suspension test | | | | | |
|---|---|---|---|---|---|---|
| | Example 1 | | | Comparison product | | |
| Species of germ | 1 h | 6 h (ppm) | 24 h | 1 h | 6 h | 24 h |
| Staph. aureus | 125 | 62.5 | 15.6 | 250 | 125 | 62.5 |
| E. coli | 250 | 62.5 | 31.2 | 1000 | 125 | 62.5 |
| Pseudomonas aeruginosa | 500 | 250 | 62.5 | 1000 | 500 | 125 |
| Candida albicans | 62.5 | 15.6 | 7.7 | 250 | 31.2 | 15.6 |
| Aspergillus niger | 500 | 250 | 62.5 | 1000 | 1000 | 250 |
| Pour point DIN 51583 | about −50° C. | | | about −20° C. | | |

| | Microbicidal action in μg/ml | |
|---|---|---|
| Desulfovibrio-desulfuricans | Example 6 | Comparison product |
| D1 | 6.25 | 6.25 |
| D2 | >200 | >200 |
| D3 | <3.1 | <3.1 |
| D39 | 50 | 100 |

| | Quantitative suspension test | | | | | |
|---|---|---|---|---|---|---|
| | Example | | | Comparison product | | |
| Species of germ | 1 h | 6 h (ppm) | 24 h | 1 h | 6 h (ppm) | 24 h |
| Staph. aureus | 125 | 62.5 | 15.6 | 250 | 125 | 62.5 |
| E. coli | 500 | 250 | 125 | 1000 | 125 | 62.8 |
| Pseudomonas aeruginosa | 500 | 250 | 62.5 | 1000 | 500 | 125 |
| Candida albicans | 125 | 62.5 | 31.2 | 250 | 31.2 | 15.6 |
| Aspergillus niger | 500 | 250 | 62.5 | 1000 | 1000 | 250 |
| Pour point DIN 53583 | about −40° C. | | | about −20° C. | | |

The improved microbicidal effects of the mixtures according to the invention in comparison with a commercially available product can be seen from the tables.

In order to achieve destruction of germs by the quantitative suspension test, substantially smaller use concentrations (ppm) of the mixtures according to the invention are required in comparison with the commercially available product. The comparatively low pour point of the mixtures according to the invention, in comparison with the commercial product, is also remarkable. This enables the combination according to the invention to be used in very cold regions, such as arise, for example, in Siberia, where agents of this type which destroy germs are used in the petroleum sector.

We claim:

1. A microbicidal agent consisting essentially of 5 to 50% by weight of the salt of a mono- or polybasic inorganic or organic acid selected from the group consisting of sulfuric acid, nitric acid, phosphoric acid, formic acid, hydrochloric acid, acetic acid, propionic acid, lactic acid, lauric acid, stearic acid, and oleic acid and an alkyl-di-guanidine of the formula

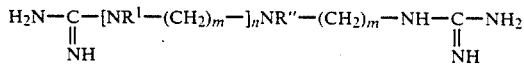

in which R' and R" denote hydrogen or $C_8$–$C_{18}$-alkyl, and R' and R" may not simultaneously be hydrogen, m denotes a number from 2 to 6 and n denotes 0 or 1, 5 to 50% by weight of a quaternary ammonium compound of the formula

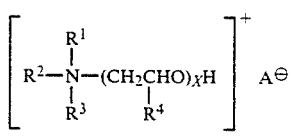

in which $R^1$ denotes $C_8$–$C_{22}$-alkyl or $C_8$–$C_{22}$-alkenyl, $R^2$ and $R^3$ denote $C_1$–$C_4$-alkyl or $C_2$–$C_3$-hydroxyalkyl and $R^4$ denotes hydrogen or methyl, or $R^1$ and $R^2$ denote $C_8$–$C_{12}$-alkyl, $R^3$ denotes $C_1$–$C_4$-alkyl or $C_2$–$C_3$-hydroxyalkyl and $R^4$ denotes hydrogen or methyl, X denotes a number from 1 to 3, and $A^-$ denotes an anion of a carboxylic acid selected from the group consisting of propionic acid, lactic acid, glycolic acid, tartronic acid, malic acid, tartaric acid, citric acid, maleic acid and benzoic acid, and, as the remainder, water, a lower alcohol, and a water-soluble glycol.

2. A microbicidal agent as claimed in claim 1, which contains a quaternary ammonium compound in which $R^1$ denotes $C_{12}$–$C_{18}$-alkyl or $C_{12}$–$C_{18}$-alkenyl, $R^2$ and $R^3$ denote methyl and $R^4$ denotes hydrogen, or $R^1$ and $R^2$ denote $C_8$–$C_{12}$-alkyl, $R^3$ denotes methyl, $R^4$ denotes hydrogen, and $A^\ominus$ denotes the anion of propionic acid, benzoic acid or lactic acid.

* * * * *